US005649016A

United States Patent [19]

Nagami et al.

[11] Patent Number: 5,649,016

[45] **Date of Patent: *Jul. 15, 1997**

[54] AUTOMATIC SOUND CONTROLLING METHOD AND APPARATUS FOR IMPROVING ACCURACY OF PRODUCING A CANCELING SOUND

[75] Inventors: Masaaki Nagami, Akashi; Kazuya Sako, Kakogawa, both of Japan

[73] Assignee: Fujitsu Ten Limited, Kobe, Japan

[ * ] Notice: The term of this patent shall not extend beyond the expiration date of Pat. No. 5,404,409.

[21] Appl. No.: 309,638

[22] Filed: Sep. 21, 1994

Related U.S. Application Data

[63] Continuation of Ser. No. 915,136, Jul. 20, 1992, Pat. No. 5,404,409.

[30] Foreign Application Priority Data

Jul. 31, 1991 [JP] Japan .................................... 3-191902
Oct. 31, 1991 [JP] Japan .................................... 3-286417

[51] Int. Cl.[6] ............................ A61F 11/06; H03B 29/00
[52] U.S. Cl. ....................................... 381/71.5; 381/71.11
[58] Field of Search ................................ 381/71, 94, 86; 181/206

[56] References Cited

U.S. PATENT DOCUMENTS 4,122,303 10/1978 Chaplin et al. .
4,153,815 5/1979 Chaplin et al. .
4,677,676 6/1987 Eriksson .................................... 381/71
4,677,677 6/1987 Eriksson .
5,022,082 6/1991 Eriksson et al. .
5,029,218 7/1991 Nagayasu .
5,093,864 3/1992 Sekiguchi et al. .
5,097,923 3/1992 Ziegler et al. ............................ 381/71
5,106,377 4/1992 Ziegler, Jr. ................................ 381/71
5,111,507 5/1992 Nakaji .
5,146,505 9/1992 Pfaff et al. ................................ 381/71
5,404,409 4/1995 Nagami et al. ........................... 381/71

FOREIGN PATENT DOCUMENTS 0098594 1/1984 European Pat. Off. .
63-311396 12/1988 Japan .
WO92/22054 12/1992 Japan .
8802912 4/1988 WIPO .

OTHER PUBLICATIONS

Eriksson, L.J. "Recursive Algorithms for Active Noise Control", International Symposium Apr. 9–11, 1991, pp. 137–146.
Eriksson, L.J. "Recursive Algorithms for Active Noise Control"; Apr. 4–11, 91, pp. 137–146, International Symposium Active Control of Sound and Vibration.
Patent Abstracts of Japan, vol. 17, No. 502 (P-1610) JP-A-51 027 680 (Fujitsu Ten Ltd) 25 May 1993.

*Primary Examiner*—Curtis Kuntz
*Assistant Examiner*—Ping W. Lee
*Attorney, Agent, or Firm*—Oliff & Berridge

[57] ABSTRACT

An automatic sound controlling apparatus including a first adaptive filter means that forms a compensating signal for canceling a stationary sound, a signal producer means that produces a predetermined shape signal based on a timing signal with respect to a sound, a second adaptive filter means that forms a compensating signal for canceling a fluctuating sound by the predetermined shape signal, whereby in the case that a sound period changes sharply, an output signal of the second adaptive filter means is output in stead of the first adaptive filter means.

10 Claims, 9 Drawing Sheets

Fig. 8

| | | | | | | |
|---|---|---|---|---|---|---|
| TRANSMISSION POSITION | P | R | N | D | 2 | L |
| SWITCH OPERATION | a | b | a | b | b | b |
| INPUT SYSTEM | FF | FB | FF | FB | FB | FB |

FF : FEEDFORWARD SYSTEM

FB : FEEDBACK SYSTEM

AUTOMATIC SOUND CONTROLLING METHOD AND APPARATUS FOR IMPROVING ACCURACY OF PRODUCING A CANCELING SOUND

This is a continuation of U.S. patent application Ser. No. 07/915,136 filed Jul. 20, 1992, now U.S. Pat. No. 5,404,409.

BACKGROUND OF THE INVENTION

1. Field of the Invention

The present invention relates to an automatic sound controlling apparatus outputting a signal with an opposite phase and an equivalent sound pressure to cancel the sound emitted from an engine etc. Particularly, this invention enables an adaptive filtering means used in the apparatus to follow the sharp attenation of a sound frequency and thereby improve the accuracy of producing the canceling sound.

2. Description of the Related Art

Conventionally, in order to reduce a sound produced from an engine etc., a passive canceling apparatus such as a muffler etc. has been used, but it is advantageous to improve said apparatus from a viewpoint of size, canceling characteristics etc. Conventionally, an active automatic sound controlling apparatus canceling a sound has output a compensating sound with an opposite phase and equivalent sound pressure from a sound source, but the frequency characteristics and stability etc. of this active automatic sound controlling apparatus per se are not sufficient, so realistic use thereof has diminished. But in recent years, as a result of expanding a frequency range to be treated owing to the development of a signal processing technique used in a digital circuit, many realistic automatic sound controlling apparatuses have been proposed (for example Japanese Unexamined Patent Publication 63-311396) such as a 2 microphones•1 speaker type active automatic sound controlling apparatus wherein a feedforward system detecting a sound by a microphone for a sound source provided at an upper stream of a duct and outputting a signal with an opponent phase and an equivalent sound pressure produced by a signal processing circuit from a speaker provided downstream of the duct, and a feedback system detecting a canceled result by a microphone for a cancelling point and feeding it back, are combined with each other. In addition an adaptive filter of this apparatus that forms the compensating sound such as a signal with an opposite phase and an equivalent sound pressure is made of a DSP (Digital Signal Processor).

On the other hand, in order to obtain a canceling effect with regard to a space with an sound source being unclear in position, for example, in a automobile room etc. it is necessary to provide a 1 microphone•1 speaker arrangement apparatus using only the feedback system without providing the microphone at the sound source.

In the above automatic sound controlling apparatus a 1 microphone•1 speaker set is provided as only the feedback of the prior art, however, in the case that the sound period of a sound source changes sharply, a problem arises in that the canceling effect is reduced since the signal delays more than the sound transfer characteristics at least from the microphone to the speaker, and is a defect of the feedback system.

Further in the case that the conventional automatic sound controlling apparatus is installed in automobiles etc. although it is difficult to provide a microphone to receive the sound as explained above, it is possible to form a sound simulating signal from an engine rotation number. However, a problem arises in that this signal is separate from a realistic signal although there is a quick response because of the signal of a feedforward system. On the other hand, a signal from a microphone as a feedback system, which is a difference signal between a muffler and a speaker, is added to a signal with an opposite phase and the equivalent sound pressure is obtained by said signal processing circuit so that it is possible to form a sound reproducing signal. However, a problem arises in that although there is the advantage that this signal is similar to a realistic signal, it is inferior to a response to a quick signal because it includes a delay characteristics. If either of the two is applied, it is difficult to improve the accuracy of the automatic sound controlling apparatus in all driving states of the automobile.

SUMMARY OF THE INVENTION

The present invention resolves the above-mentioned problem and provides an automatic sound controlling apparatus following the sharp change of a sound period and forming a signal that is similar to a realistic signal and superior to a response.

The present invention provides an automatic sound controlling apparatus including an electric signal•sound converter outputting a compensating sound to a canceling object space to cancel a sound from a sound producing source and a sound•electric converter for converting a residual sound of the sound canceling with a compensating signal from the electric•sound converter into an electric signal, characterized in that it comprises a first adaptive filtering means that controls filter coefficients based on a signal from the sound•electric converter forming a compensating signal to the electric•sound converter for canceling a stationary sound, a transfer characteristics simulating means that simulates transfer characteristics of the electric•sound converter, the sound•electric converter and the sound of the canceling object space, a difference signal calculating means that calculates a difference signal between outputs of the sound•electric converter and the transfer characteristics simulating means to supply the first adaptive filtering means with the difference signal, a signal producing means that produces a predetermined shape signal based on a timing signal with respect to a sound producing period of the sound producing source, a second adaptive filtering means that controls filter coefficients based on a signal from the sound•electric converter forming a compensating signal to the electric•sound converter for canceling a fluctuating sound, an adding means that adds an output signal of the first adaptive filtering means and an output signal of the second adaptive filtering means to output the adding signal to the electric•sound converter and the transfer characteristics simulating means.

With the above construction in the stationary state, and a sound period of the sound producing source is about constant, the sound in the canceling object space, such as a muffler, is canceled by the sound with the opposite phase and the equivalent sound pressure from the electric•sound converter. The residual sound is detected by the sound•electric converter and the electric signal is input to the coefficient renewal means of the first adaptive filtering means. The input signal is minimized by the least squares method so that the filter coefficients are set to the first adaptive filtering means. The signal from the sound•electric converter is added to the reversed signal from the transfer characteristics simulating means at the difference signal calculating means so that the reproducing signal is made. The reproducing signal is the input signal of the first adaptive to form a revised signal to the electric•sound converter, in the fluctuating state and the sound period changes in the first adaptive filtering means, a transfer delay occurs. The fundamental frequency signal and the harmonic frequency signal is produced by the timing signal of the signal produced during the sound producing period of the sound producing source and input to the second adaptive filtering means. The filter coefficients of the second adaptive filtering means are revised based on the residual sound of the electric•sound converter to make the compensating signal and the compensating signal is output to electric•sound converter so that the transfer delay is reduced and, at the fluctuating state, the canceling effect is improved.

Further, the present invention provides an automatic sound controlling apparatus including an electric signal•sound converter outputting a compensating sound to a canceling object space to cancel a sound from a sound producing source and a sound•electric converter for converting a residual sound of the sound canceling with a compensating signal from the electric•sound converter into an electric signal to form an error signal because of the residual sound, characterized in that it comprises an adaptive filtering means that controls filter coefficients based on the error signal from the sound•electric converter forming a compensating signal to the electric•sound converter for canceling a stationary sound, a transfer characteristics simulating means that simulates transfer characteristics for adding the error signal to the compensating signal as an output signal of the adaptive filtering means to form an input signal of the adaptive filtering means, an adding means that adds the error signal and an output signal of the transfer characteristics simulating means, and a switch that alternatively selects a signal indicating the rotation number of an engine, a signal indicating the ignition timing of the engine, an output of the adding means as an input signal of the adaptive filtering means, and in the case that the transmission position of the engine is in a no load state of the engine, the switch supplying the adaptive filtering means with the signal showing the rotation number of the engine or the signal showing the ignition timing, and in the case that the transmission position of the engine is in a load state of the engine the switch supplying the adaptive filtering means with the output of the adding means.

Also, an automatic sound controlling apparatus may include, additionally, a harmonic wave producing means that produces a harmonic wave signal of the sound based on the signal showing the rotation number of the engine or the signal showing the ignition timing.

With the above construction in the no load state of the transmission position of an automobile with a stop, the signal showing the rotation number or the signal showing the ignition timing of the engine is output to the adaptive filtering means by the switch. At this time even if the rotation number increases sharply by stepping on the accelerator, the controlling signal by these signals or the harmonic wave signal is small in the time delay to be formed so that the error owing to the time delay is small. Also in a load state of the transmission position of the engine, the output of the adding means is output to the adaptive filtering by the switch, but at this time even when stepping on the accelerator the rotation number does not increase sharply for the adding load as described above so that the time delay is allowed and the output signal to the adaptive filtering means is as realistic as possible and small in error. Also, the time of driving, when the rotation number changes sharply, the signal showing the rotation number of the engine or the ignition timing of the engine or the output of the harmonic wave producing means is provided to prevent the time delay. When driving at a constant velocity, the realistic signal is provided from the adding means to improve the accuracy of the apparatus as a whole.

BRIEF DESCRIPTION OF THE DRAWINGS

FIG. 8 is a view explaining the operation of switching a switch 75 in FIGS. 3 and 4;

DESCRIPTION OF THE PREFERRED EMBODIMENTS

The invention will be described in greater detail with reference to specific embodiments thereof and accompanying drawings.

Figure 1:
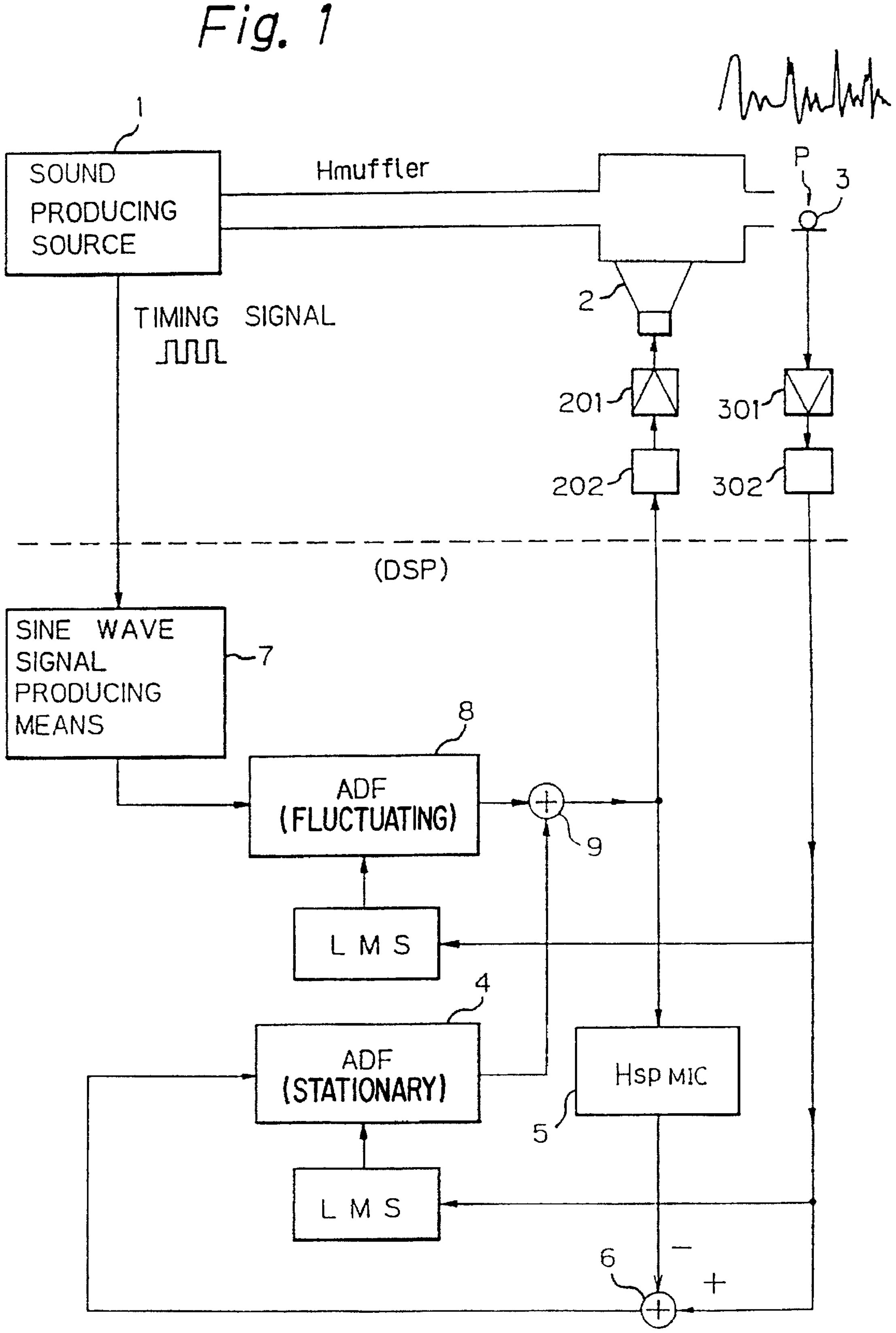
FIG. 1 is a view of an automatic sound controlling apparatus according to a first embodiment of the present invention.

FIG. 1 is a view of an automatic sound controlling apparatus according to a first embodiment of the present invention. The construction of the apparatus will be described by referring to FIG. 1. The apparatus includes a speaker 2 fitted to a muffler where a sound from a sound producing source 1 such as a engine, a motor etc. arrives through an exhaust pipe to cancel the sound, a amplifier 201 connected to said speaker 2, a digital to analog converter (D/A) 202, a microphone 3 for converting a residual sound by canceling the sound from the sound producing source 1 with the sound from the speaker 2 into an electric signal, an amplifier 301 connected to said microphone 3, an analog to digital converter (A/D) 302, a first adaptive filtering means 4 inputting a signal from a difference signal calculating means 6 as explained herebelow and forming a compensating signal for outputting to the speaker 2 and canceling a stationary signal based on a signal from the A/D converter 302, a transfer characteristics simulating means 5 for simulating sound transfer characteristics ($H_{SPMIC}$) of the speaker 2, the microphone 3 and a canceled object space, a difference signal calculating means 6 for calculating a difference signal between an output of the microphone 3 and an output of the transfer characteristics simulating means 5 and supplying the first adaptive filtering means with the difference signal, a signal producing means 7 for producing a fundamental signal of a sine wave or a harmonic signal of the fundamental signal based on a rotation timing signal or an ignition timing signal obtained by the sound producing source 1, for example, a detector for a rotation number or an ignition timing controlling apparatus, a second adaptive filtering means 8 inputting a signal from the signal producing means 7 and forming a compensating signal for outputting to the speaker and for canceling a fluctuating sound, an adding means 9 for adding an output of the first adaptive filtering means 4 and an output of the second adaptive filtering means 8 and outputting the adding signal to the speaker 2 and the transfer characteristics simulating means 5.

In this place, the first and second adaptive filtering means 4, 8, the transfer characteristics simulating means 5, the difference signal calculating means 6, the signal producing means 7 and the adding means are made from the DSP (Digital Signal Processor).

Figure 2:
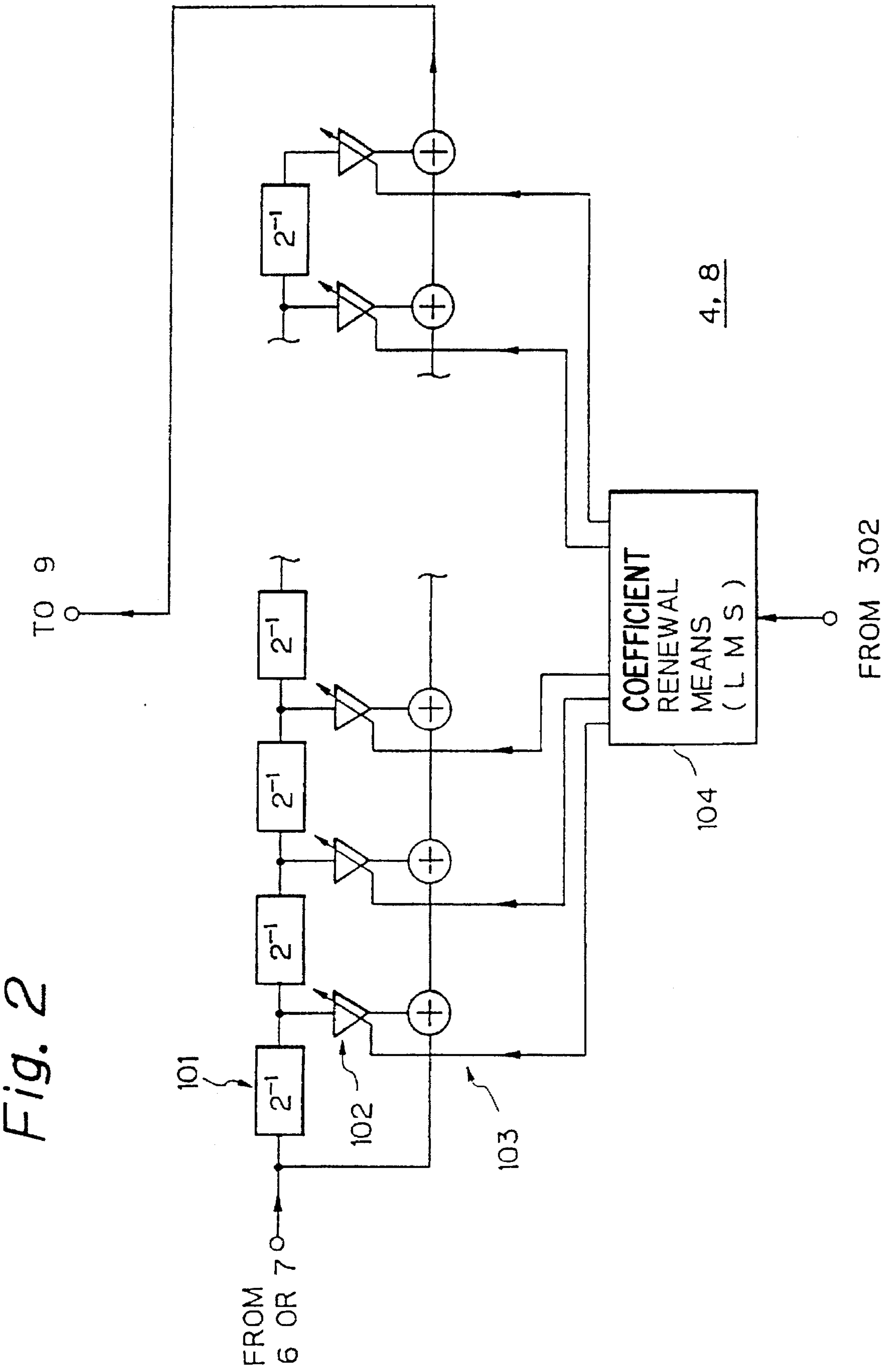
FIG. 2 is a view showing the construction of an adaptive filtering means in FIG. 1.

FIG. 2 is a view showing the construction of an adaptive filtering means in FIG. 1. Referring to FIG. 2, the adaptive filtering means 4, 8 includes a series of delay devices 101 for delaying a sampling period respectively, a plurality of multipliers 102 connected to each output of the delay devices 101, a plurality of adders for adding each output of the multipliers 102 and a coefficient renewal means 104 for controlling a coefficient of each of the multipliers 102 to minimize an output of the A/D converter 302 by the least squares method. In addition, a transfer function of the transfer characteristics simulating means 5 is equalized initially.

The operation of the apparatus set forth above will be discussed herebelow. In the stationary case that the engine, as the sound producer 1, rotates at a constant speed in the canceling object space of the muffler, the compensating sound wave with an opposite phase and equivalent sound pressure is output from the speaker 2, the incompletely canceled residual sound is converted into an electric signal by the microphone 3; this signal inputs the coefficient renewal means of the first adaptive filtering means 4 through the amplifier 301 and the A/D converter 302. In order to minimize the input signal of this coefficient renewal, this coefficient renewal means, and multiplication coefficients of finite impulse response type multipliers (FIR) constructing the first adaptive filtering means 4 are revised so that the input signal of the first adaptive filtering means 4 is adjusted to be a compensating signal and the compensating signal is output to the speaker 2 through the adder means 9, the D/A converter 202 and the amplifier 201. This compensating signal is shaped through the transfer characteristics simulating means 5, reversed, and added to the residual signal from the microphone 3 in the difference signal calculating means 6 to form the reproducing signal and is fedback to the input of the adaptive filtering means 4. In this way, in the stationary state, the feedback system centering the first adaptive filtering means 4 allows a sound with a fundamental frequency produced at the sound producing source 1 and a harmonic frequency produced at the muffler, the exhaust pipe etc. to be canceled.

In a fluctuating state in which the rotation number sharply increases and decreases (when racing), the feedback system centering said first adaptive filtering means 4 has a delay corresponding to the transfer characteristics $H_{SPMIC}$ of the transfer characteristics simulating means 5 and reduces the canceling effect. In such a fluctuating state, in the sine wave signal producing means 7 a sine wave signal is produced, inputted to the second adaptive filtering means 8 to form a compensating signal and the compensating signal is outputted to the speaker 2 through the adder means 9, the D/A converter 202 and amplifier 201. A residual signal from the microphone 3 is input to a coefficient renewal means of the second filtering means 8 through the amplifier 301, the A/D converter 302. In this coefficient renewal means, in the same way as above, said multiplication coefficient is revised to minimize the level of input signal thereof by the least squares method and the input signal of the second adaptive filtering means 8 is adjusted to be a compensating signal.

In this way in the fluctuating state, a simulating signal as a sound signal is made of a timing signal from the sound producing source 1 so that since the feedforward system centers the second adaptive filtering means 8 inputting the simulating signal, the canceling effect due to the fluctuation of the sound fundamental frequency, which cannot be obtained in the first adaptive filtering means 4, may be easily obtained. Said sine wave signal producing means 7 produces not only a sine wave signal but also a harmonic wave signal so that it is possible to cancel a harmonic wave sound produced at the muffler etc.

In this way since the second adaptive filtering means 8 is added to the apparatus so that it is possible to ensure the canceling effect not only in the stationary state but also in the fluctuating state of the sound period of the sound producing source 1. In addition, the timing signal may be extracted not only from the detector of the engine rotation number or the ignition timing controlling apparatus but also, for example, from a vibrometer positioned in a sound transfer passage (for example muffler) extending, for example, from the sound producing source 1 to the sound•electricity converter 3.

As set forth above according to the present invention, in the case that the sound period of the sound producing source changes sharply, the adaptive filtering means forming the simulating signal owing to the timing signal of the sound producing source and the compensating signal of the sound signal is provided additionally so that the automatic sound controlling apparatus may follow the sharp frequency change of the sound.

Figure 3:
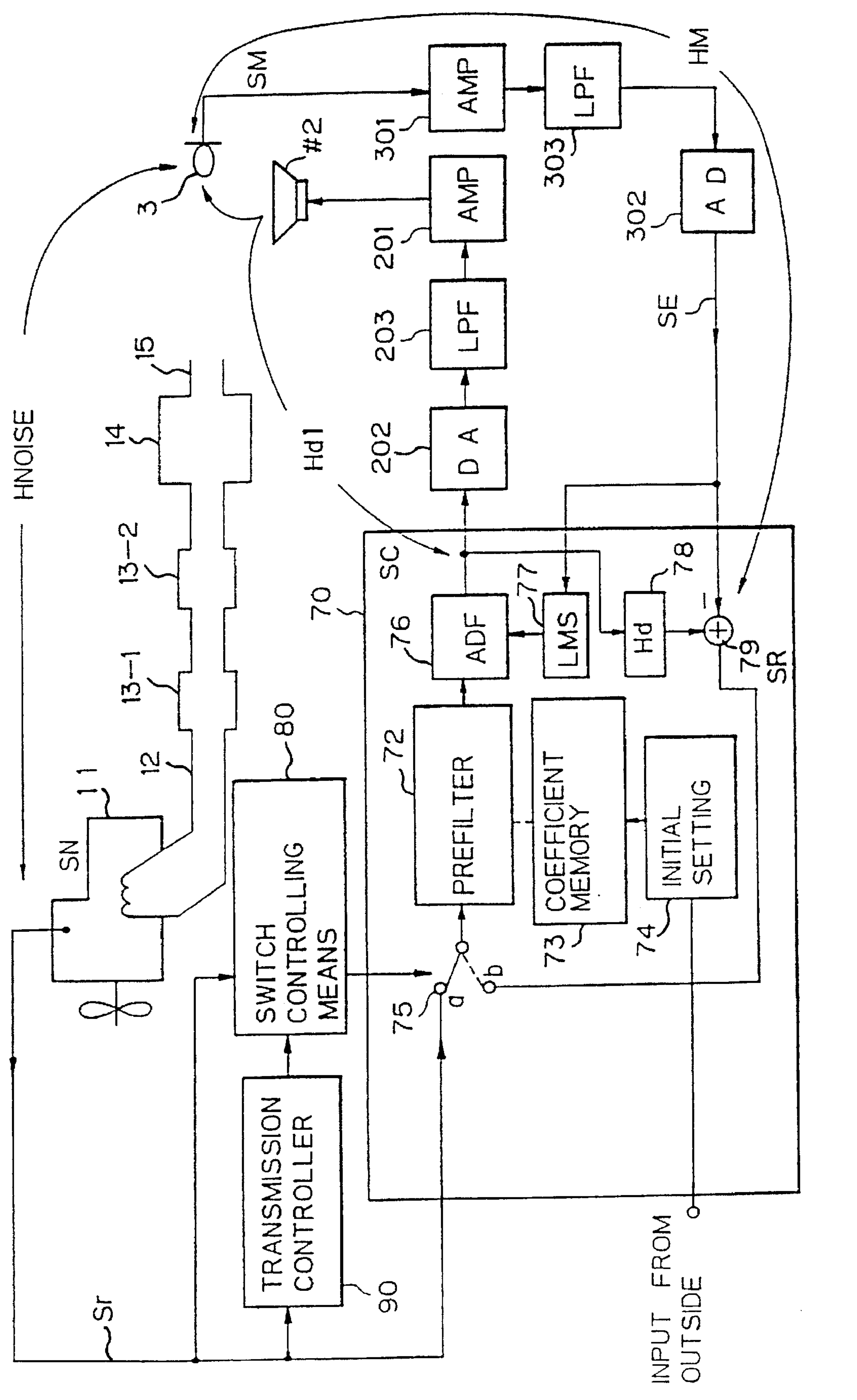
FIG. 3 is a view of an automatic sound controlling apparatus according to a second embodiment of the present invention.
Figure 4:
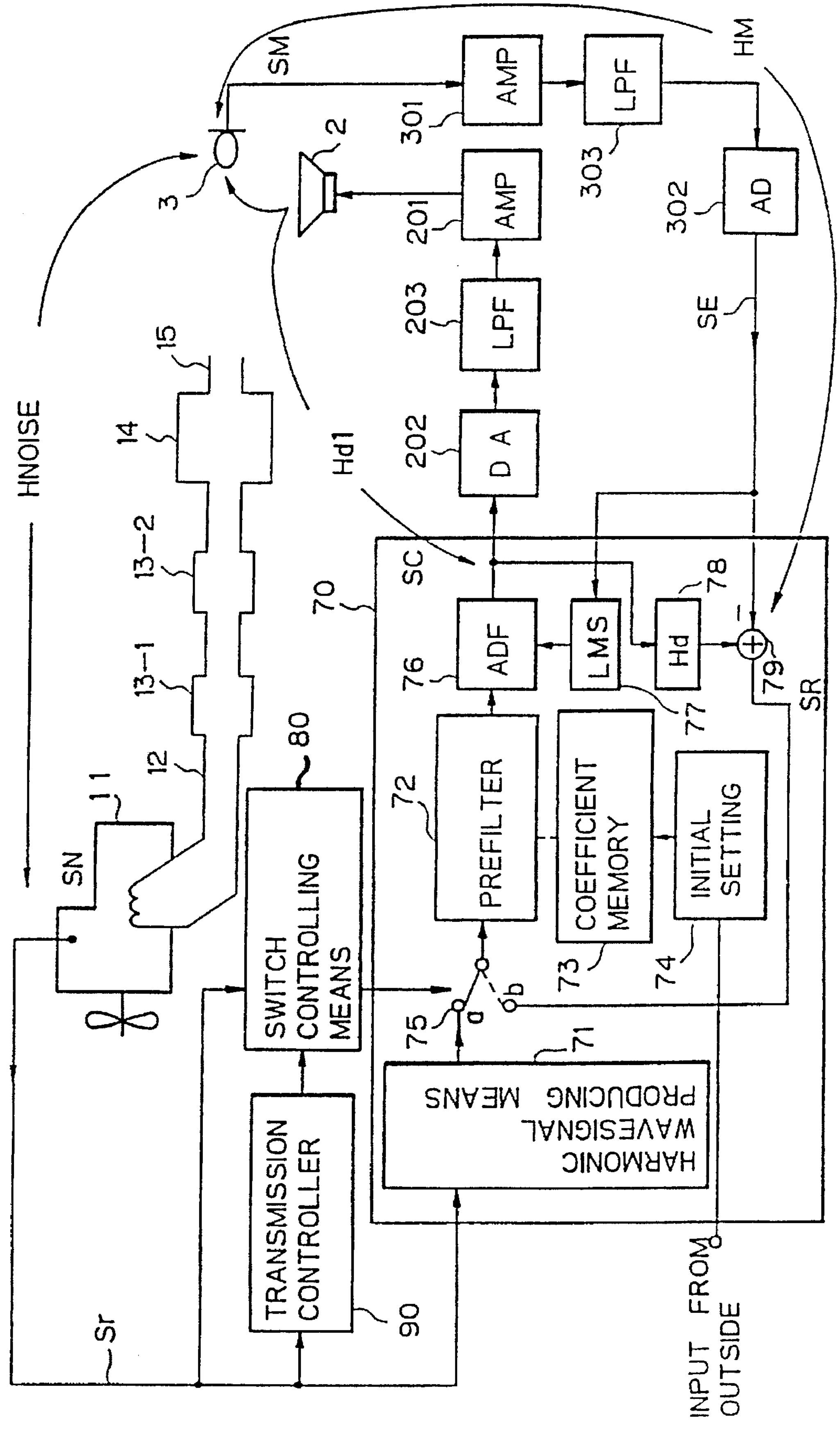
FIG. 4 is a view of an automatic sound controlling apparatus according to a third embodiment of the present invention.

FIGS. 3 and 4 are views of an automatic sound controlling apparatus according to second and third embodiments of the present invention. FIGS. 3 and 4 are different in the point concerning whether or not a harmonic wave producing means 7 is provided. Referring to FIGS. 3 and 4, overall constructions of the apparatus will be discussed. A controlled object of the apparatus includes an engine 11 of an automobile, an exhaust pipe 12 for discharging exhaust gas of the engine 11 in the atmosphere, submufflers 13-1 and 13-2 in which the pressure of the exhaust gas is reduced gradually in the exhaust pipe to restrain sound production before the exhaust gas is discharged in the atmosphere and a sound owing to the reduced exhaust gas is reflected by a wall of the exhaust pipe, the reflected sounds interfere with each other and are canceled, a main muffler 14 following the submufflers 13-1 and 13-2 with the same object as above, a tail pipe 15 connected to the main muffler 14 to discharge the exhaust gas in the atmosphere. The apparatus includes a compensating signal producing means 70 for producing a controlled signal with regard to a sound of a feedforward system based on the rotation number of the engine 11 to form a compensating signal, a digital to analog converter 202 for converting a digital signal from the compensating signal producing means 70 into an analog signal, a low pass filter 203 connected to the digital to analog converter 202 to remove a harmonic wave signal, a power amplifier 201 connected to the low pass filter 203, a speaker 2 driven by a sound from the power amplifier 201 to discharge a sound and cancel a sound from the tail pipe, a microphone 3 that catches the result of canceling the sound from the tail pipe with the speaker 2 to convert an electric signal, an amplifier 301 connected to the microphone 3, a low pass filter 303 connected to the amplifier 301, an analog to digital converter 302 connected to the low pass filter 303 to convert same into an analog signal into a digital signal so that the converted signal is used as feedback control and controlled signals of the compensating signal producing means 70, a switch controlling means 80 that inputs a shift signal in position of a transmission output from a transmission controller 90 or a rotation number signal of the engine 11 to switch a controlled signal for forming a compensating signal based on the changing degree of the shift signal or the rotation number signal, the transmission controller 90 switching a gear ratio automatically based on the rotation number of the engine 11 or a velocity signal of an automobile. The compensating signal producing means 70, as shown in FIG. 3, includes a prefilter 72 for equalizing the frequency characteristics of the submufflers 13-1, 13-2 and the main muffler 14 in advance, a coefficient memory 73 for providing the prefilter 72 with a coefficient, an initial setting circuit 74 for setting the measured coefficient of the submuffler 13-1, 13-2 and the main muffler 14 to the coefficient memory 73 from outside, a switch 75 provided at the input side of the prefilter 72, one terminal (a) of which inputs a signal showing the rotation number or a signal showing the ignition timing Sr as a feedforward signal, the other terminal (b) of which inputs a feedback signal as explained herebelow, and these two terminals of which are switched by the switch controlling means 80, an adaptive filtering means 76 that inputs a signal from the prefilter 72 as a controlled signal and outputs a compensating signal to the digital to analog converter 202, a minimization means 77 that sets the coefficient to the adaptive filter means 76 to minimize an error signal from the analog to digital converter 302, transfer characteristics simulating means 78 connected to the output of the adaptive filtering 76 and simulating a transfer characteristics Hd from the adaptive filtering 76 through the digital to analog converter 202, the low pass filter 203, the power amplifier 201, the speaker 2, the microphone 3, the amplifier 301, the low pass filter 303 to the analog to digital converter 302, and an adder means 79, the output of which is connected to the other input terminal of the switch 75 to add the reversed output of the transfer characteristics simulating means 78 and the output of the analog to digital converter 302.

In addition, the signal showing the rotation number of the engine 11 is taken out from a sensor fitted to a rotary axis such as a crankshaft, also the signal showing the ignition timing is taken out from, for example, a distributor. Also, as shown in FIG. 4, a harmonic wave producing means 71 in which a signal Sr showing the rotation number of the engine 11 or a signal Sr showing the ignition timing of the engine is used as a fundamental signal so that these harmonic wave signals are produced, is provided to input a signal of the harmonic wave signal producing means 71 to the one terminal of the switch 75.

Figure 5:
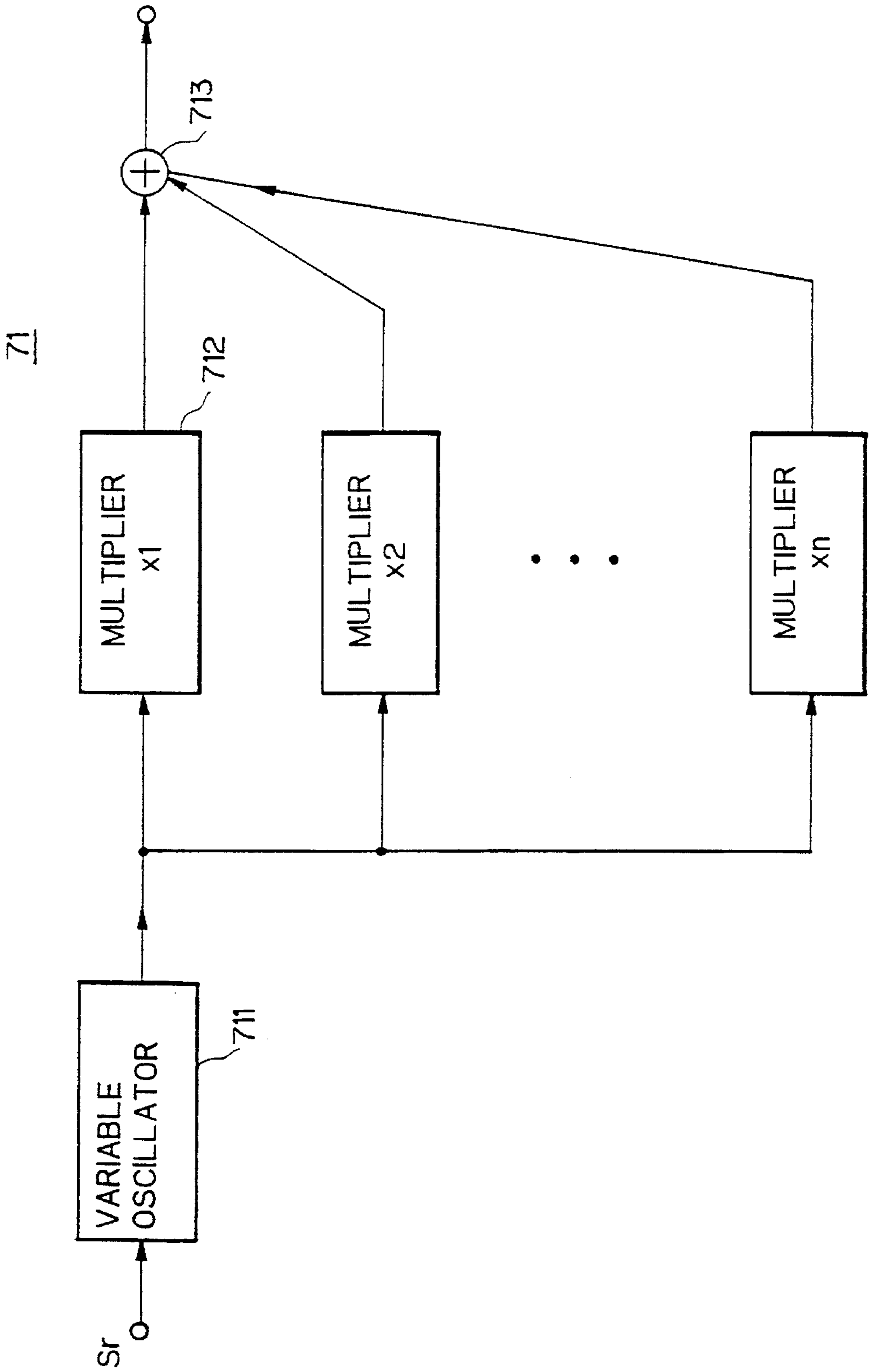
FIG. 5 is a view showing the construction of a harmonic producer in FIG. 4.

FIG. 5 is a view showing the construction of a harmonic producer in FIG. 4. Referring to FIG. 5, the harmonic wave signal producing means 71 includes a variable frequency oscillator 711 that forms a sound with a frequency corresponding to the rotation number or the ignition timing of the engine 11, a plurality of multipliers 712 for multiplying the frequency of the output of the variable frequency oscillator 711, and an adder means 713 for adding the outputs of a plurality of multipliers 712 to output the added signal to the prefilter 72.

Figure 6:
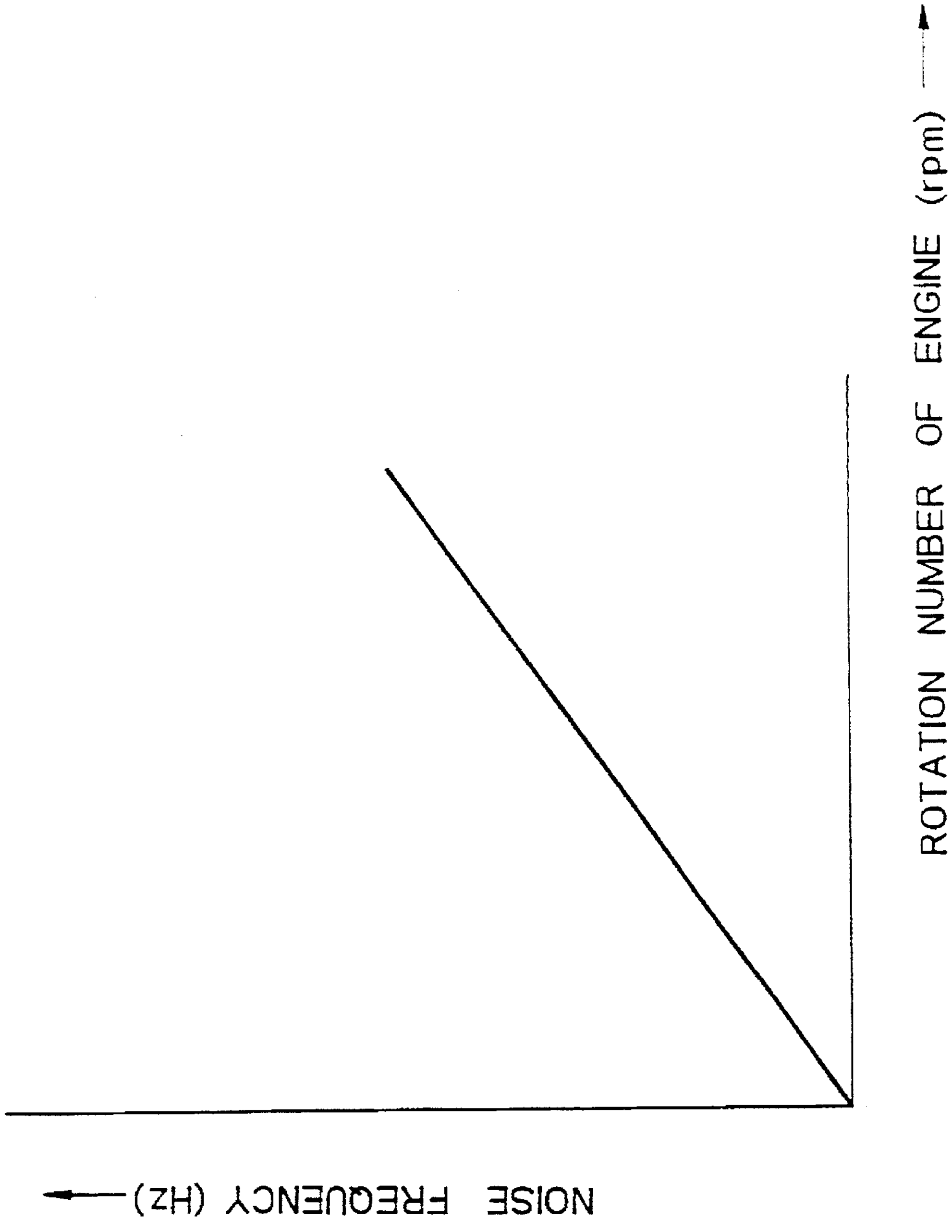
FIG. 6 is a view showing the relation between the engine rotation number and the sound frequency in a variable frequency oscillator of FIG. 5.

FIG. 6 is a view showing the relation between the engine rotation number and the sound frequency in a variable frequency oscillator of FIG. 5. Referring to FIG. 6, the sound source of the engine 11 is an assembly of harmonic components such as the first order, the second order, the third order, . . . , the nth order depending on the rotation number, and the harmonic components increase together with the rotation number increment. In the variable frequency oscillator 711 shown in FIG. 5, in order to produce the above sound, the rotation number of the engine 11 and the sound frequency from the tail pipe are measured in advance to obtain the relation as shown in this Figure and the signal with the frequency corresponding to the rotation number of the engine 11 is produced to output it to the following multipliers 712. In this way, the harmonic components included in the real produced sound of the engine 11 are made with high accuracy, and since pulse shapes showing the real rotation number of the engine 11 partly includes the harmonic wave signal, by using the pulse shape directly, the same effect as above may be expected to some degree. In addition the signal showing ignition timing is normally a signal that multiplies the signal showing the rotation number.

Figure 7:
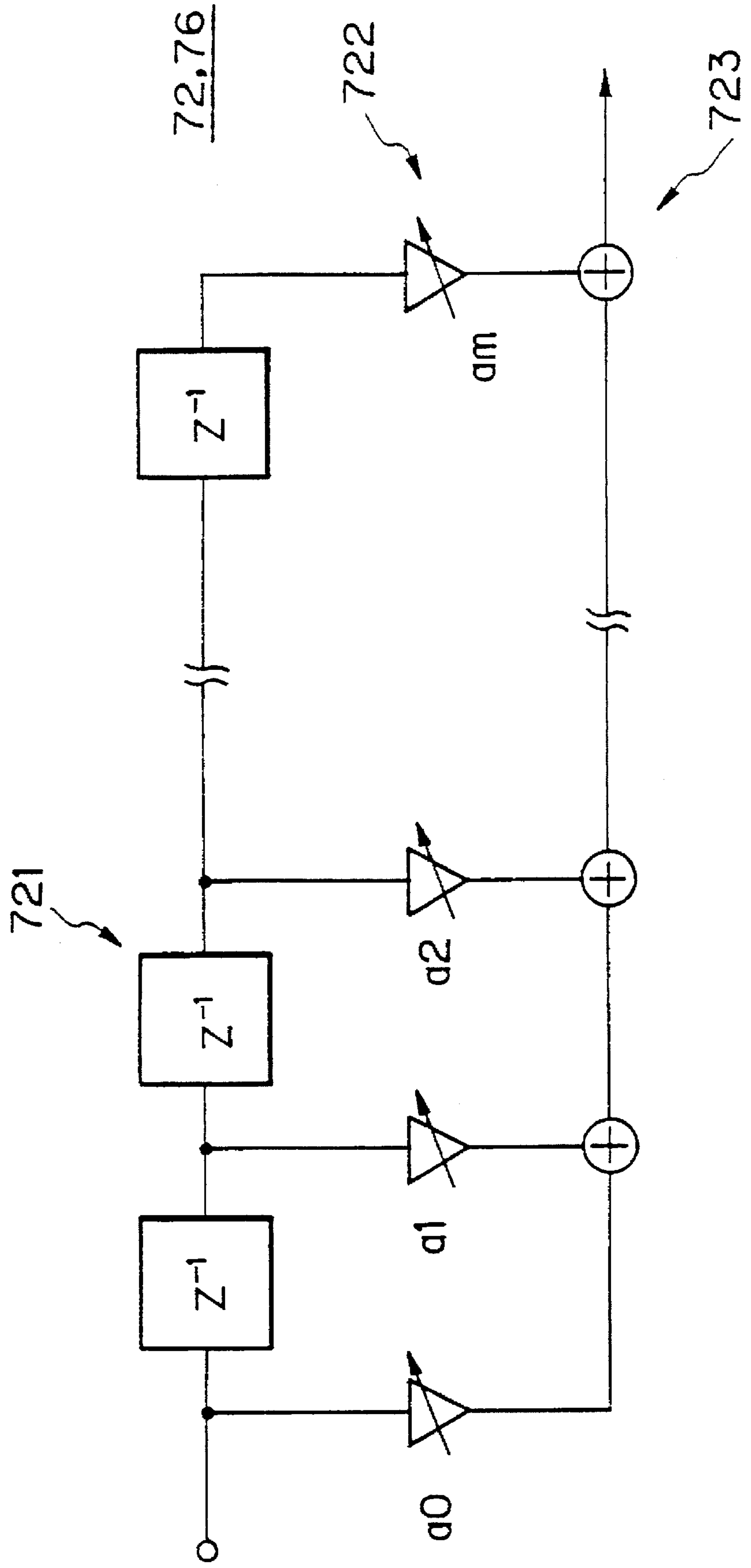
FIG. 7 is a view showing a construction of a prefilter and an adaptive filter in FIGS. 3 and 4.

FIG. 7 is a view showing the construction of a prefilter and an adaptive filter in FIGS. 3 and 4. Referring to FIG. 7, the prefilter 72 and the adaptive filtering means 76 are common in construction but different in setting a coefficient. Both the prefilter 72 and the adaptive filtering means 76 include a plurality of delay devices 721 delaying an input signal every sampling period, a plurality of variable multipliers 722 that accept the input signal and are connected to the output of each of the delay devices, a plurality of adding means 723 connected to each of the variable multipliers 722. Coefficients a0, a1, a2, . . . , am of each of the variable multipliers are variable owing to being supplied by the coefficient memory 73 and the minimization means 77.

Now let the sampling frequency be fs, a sampling period is $$T=1/fs.$$

Further let the input signal be x(t)=exp(jωt), an output signal y(t) is shown as follows.

$$\begin{aligned} y(t) &= a0\cdot\exp(j\omega t)+a1\cdot\exp\{j\omega(t-T)\}+ \\ &\quad a2\cdot\exp\{j\omega(t-2T)\}+\ldots+am\cdot\exp\{j\omega(t-mT)\} \\ &= \exp(j\omega t)\cdot[a0+a1\cdot\exp(-j\omega T)+ \\ &\quad a2\cdot\exp(-j2\omega T)+\ldots+am\cdot\exp(-jm\omega T)] \end{aligned}$$

In one of the prefilters 72, the frequency characteristics of the submuffler 13-1, 13-2 and the main muffler 14 are measured in advance so that on the basis of this measurement the coefficients a0, a1, a2, . . . , am of each of the variable multipliers 722 in the above equation are set to the initial setting circuit 74 and the coefficient memory 73.

On the other hand, in the case of the adaptive filtering 76, the coefficients are supplied by the minimization means 77. Next the minimization means will be discussed. In the equation letting the input signal be x(nt)=exp (−jnωT), and letting the coefficients be ak(n), each of the coefficients ak(n) is obtained from the following convergence equation.

$$ak(n+1)=ak(n)+\alpha\cdot e(n)\cdot x(n-k)/|x(n)|^2$$

$$\begin{aligned} |x(n)|^2 &= \sum_{i=1}^{m} x(n-i)^2 \\ &= \{x(n)^2+x(n-1)^2+x(n-2)^2+\ldots+x(n-m)^2\}/m \end{aligned}$$

In this equation e(n) shows an error signal that is an output signal of the analog to digital converter 302 and α shows a convergence constant. It takes a predetermined time to cause the coefficient ak(n) to converge at a constant. Accordingly, as explained above an influence of the main muffler 4 etc. is removed from the adaptive filtering means 76 to reduce the load of the adaptive filtering 76, while since a constant convergence time is needed, it would be difficult to process within the convergence time when the change of the rotation number of the engine 11 is large.

Next the producing signal SR of the feedback system input to the other terminal of the switch 75 will be discussed. Now let the sound signal produced by the engine 11 be SN, let the the output signal be SC, let the output of the microphone 3 be SM, and let the output of the adding means 79 be SR. Also let the transfer characteristics from the engine 11 to the microphone 3 be HNOISE, let the transfer characteristics from the adaptive filtering 76 to the microphone 3 be Hd1, let the transfer characteristics from the microphone 3 to the adding means 79 be HM, and let Hd be Hd=Hd1•HM, the output signal SM of the microphone 3 is expressed as follows.

$$SM = SN \cdot HNOISE + SC \cdot Hd1$$

And the output signal of the adding means SR is expressed as follows.

$$\begin{aligned} SR &= SM \cdot HM - SC \cdot Hd \\ &= (SN \cdot HNOISE + SC \cdot Hd1 - SC \cdot Hd1) \cdot HM \\ &= SN \cdot HNOISE \cdot HM \end{aligned}$$

Therefore a signal obtained when only a sound is detected by the microphone 3 may be calculated.

Next the output signal SE of the analog to digital converter 302 is given as a control signal for making the coefficient renewal by the minimization means 77 of the adaptive filtering means 76. The adaptive filtering means 76 makes the coefficient renewal so that this control signal level becomes zero, so since SE=SM•HM, SM=0, SE=0. Accordingly the output signal SR from the adding means 79 is input to the adaptive filtering means 76 as a controlled signal and the output signal SE is input to the minimization means 77 from the analog to digital converter 302 as a controlling signal so that the output signal SE is calculated to be zero in the adaptive filtering means 76 in order to output a compensating signal SC.

The foregoing will be discussed in the same way with regard to the feedforward system.

FIG. 8 is a view explaining the operation of switching a switch 75 in FIGS. 3 and 4. Referring to FIG. 8, the switch controlling means 80 obtaining the transmission shift position signal from the transmission controller 90 makes the switch 75 connect to the switch terminal (a) side when the transmission shift position is in a no load state such as P range for parking or N range for neutral as shown in this Figure. However when the transmission shift position is in a load state such as R, D, 2 and L, the switch 75 is connected to the output (switch terminal b side) of the adding means 79. Therefore when in a no load state, the adaptive filtering means 76 inputs a controlled signal of the feedforward system, and when in a load state, it inputs a controlled signal of the feed back system. In a no load state because of the revving up the engine, the change of the rotation number is too large, but in this case, since the controlled signal of the feedforward system is input to effect a short delay, it is possible to prevent accuracy deterioration owing the delay for processing a signal. On the other hand, in the load state, since the rotation number does not change sharply such as when revving up the engine in a no loading state, the signal processing delay is allowed and the realistic controlled signal is used to improve accuracy thereof.

Figure 9:
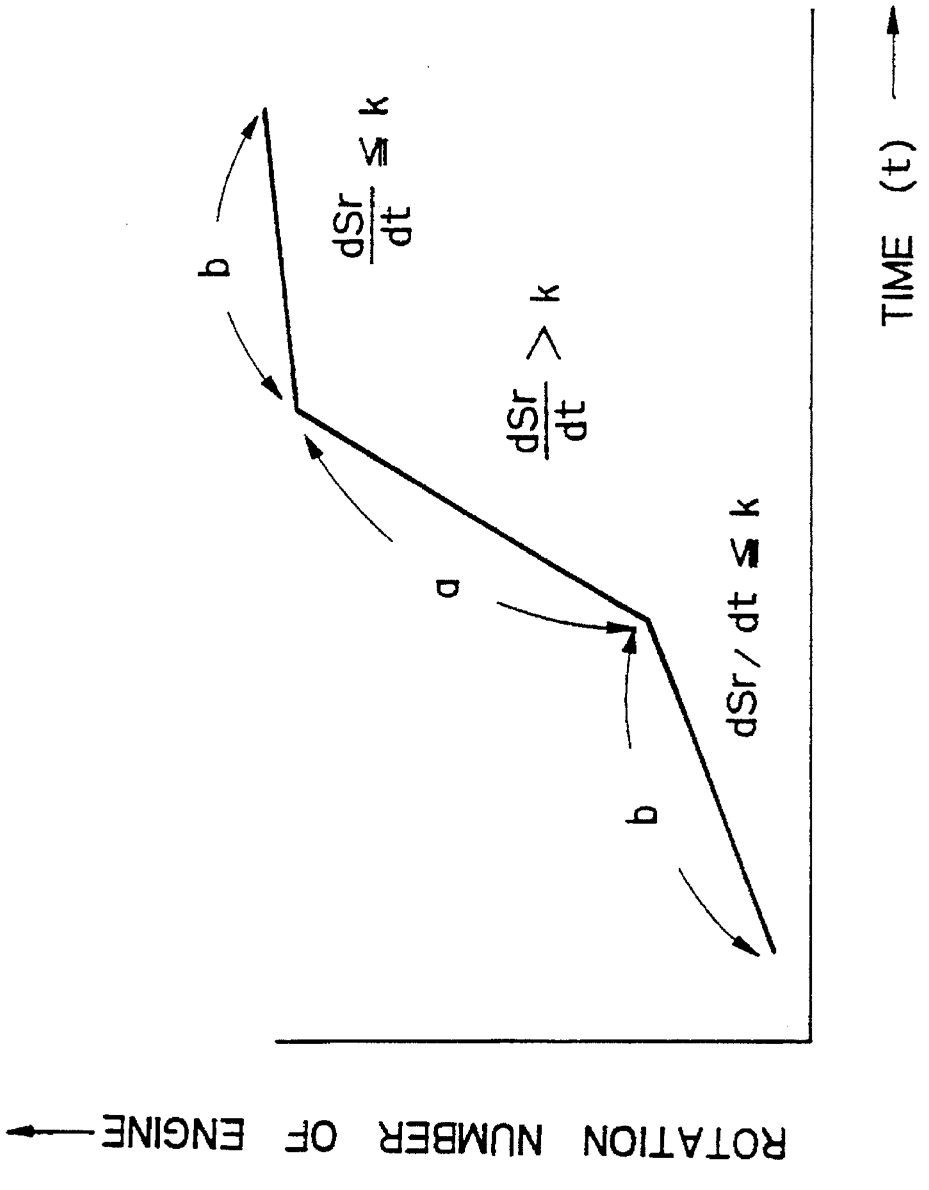
FIG. 9 is a view explaining the operation of switching a switch 75 in FIGS. 1 and 4 depending on the change of the engine rotation number.

FIG. 9 is a view explaining the operation of switching a switch 75 in FIGS. 1 and 4 depending on the change of the engine rotation number. Referring to the FIG. 9, the switch controlling means 80 shown in FIGS. 3 and 4 obtains a change of the rotation of the engine 11 as dSr/dt as shown in FIG. 9. When the value of the change is larger than a predetermined value k, the adaptive filtering means 76 is connected to the switch terminal (a) side by the switch 75. When the value of the change is smaller than k, the switch terminal is connected to (b) side by the switch 75 to connect the adaptive filtering means to the adding means 79. Thereby, when the automobile is driven at a constant low or high speed, a delay time is allowed to process a signal since a sound change is small, and the adaptive filtering means 76 inputs the controlled signal of the feedback system and uses the realistic signal to improve accuracy thereof. Further in return [compensation] for not allowing a processing delay when velocity changes, the adaptive filtering means 76 inputs a signal somewhat apart from the realistic signal, but if the change of the sound is large it is possible to improve accuracy with a short delay controlling signal.

In addition, when the switch 75 is connected to the terminal (a) side, and when the convergence constant $\alpha$ is larger, the convergence as expressed above becomes faster and the delay time becomes shorter. On the contrary when the switch 75 is connected to the terminal (b) side it is possible to take a slow convergence in order to improve the accuracy when the velocity does not change. Also, either of the switching controls of the switch 75 by the position of the transmission and by the change of the rotation number of the engine 1 may be performed individually. Further the transmission controlling means 90 may provide the position of the shift lever so that it may output a signal showing the position of the transmission and is not especially limited to the automatic transmission.

As set forth above, according to the present invention, in an automatic sound controlling apparatus including an adaptive filter that makes the coefficient renewal minimize the error signal to form the opposite characteristics of the sound, when the rotation number of the engine changes sharply, a signal with a short delay but somewhat unrealistic is used as a control signal and when the change of the rotation number is small, a signal with a somewhat large delay but realistic is used as a control signal so that it is possible to improve the accuracy of the adaptive filtering means.

We claim:

1. An automatic sound controlling apparatus for improving accuracy of producing a canceling sound comprising:

an electric-signal-to-sound converter outputting a compensating sound to a canceling space to cancel a sound from a sound-producing source;

a sound-to-electric-signal converter for converting a residual sound in the canceling space into an electric signal to form an error signal based on the residual sound;

adaptive filtering means that controls filter coefficients based on the error signal from the sound-to-electric-signal converter to form a compensating signal that is supplied to the electric-signal-to-sound converter;

transfer characteristics simulating means that simulates transfer characteristics in the canceling space and receives the compensating signal from the adaptive filtering means;

adding means that adds the error signal and an output signal of the transfer characteristics simulating means;

a switch that alternatively feeds first and second signals to the adaptive filtering means, the first signal representing characteristics of the sound-producing source, and the second signal being an output of the adding means; and a prefilter provided for said adaptive filtering means before forming said compensating signal to equalize frequency characteristics of at least one of a main muffler and submufflers, wherein the frequency characteristics of the main muffler and the submufflers, coupled in serial to an engine, are measured in advance, so that on the basis of this measurement the coefficients of the prefilter are set to an initial setting circuit and a coefficient memory.

2. An automatic sound controlling apparatus for improving accuracy of producing a canceling sound comprising:

a sound making device for outputting a compensating sound in a canceling space to cancel undesired sound from a sound-producing source;

a sound receiving device for producing an error signal that represents a difference between said compensating sound and said undesired sound;

an adaptive filter that forms a compensating signal for attenuation of said undesired sound, said compensating signal being based on said error signal produced from said sound receiving device and being supplied to the sound making device; and a prefilter provided for said adaptive filter, said prefilter equalizing frequency characteristics of at least one of a main muffler and a submuffler before forming said compensating signal.

3. The automatic sound controlling apparatus for improving the accuracy of producing the canceling sound of claim 2, further comprising a transfer characteristics simulator for simulating transfer characteristics in the canceling space and receiving the compensating signal from the adaptive filter.

4. The automatic sound controlling apparatus for improving the accuracy of producing the canceling sound of claim 3, further comprising an adder for adding the error signal and an output signal from the transfer characteristics simulator to allow an output signal of said adder be applied to said prefilter.

5. The automatic sound controlling apparatus for improving the accuracy of producing the canceling sound of claim 4, further comprising a switch that alternatively feeds first and second signals to the prefilter, the first signal representing characteristics of the sound-producing source, and the second signal being an output of the adder.

6. A method for canceling undesired sound from a sound-producing source comprising:

outputting a compensating sound in a canceling space with a sound making device to cancel said undesired sound;

producing an error signal from a sound receiving device that represents a difference between the compensating sound and said undesired sound;

forming a compensating signal for attenuation of said undesired sound, said compensating signal being based on said error signal produced from said sound receiving device and being supplied to said sound making device; and equalizing frequency characteristics of at least one of a muffler and a submuffler before forming said compensating signal.

7. The method of claim 6, further comprising receiving the compensation signal from an adaptive filter and providing a simulated transfer characteristics signal in the canceling space and adding the error signal and said simulated transfer characteristics signal to define an addition signal.

8. The method of claim 7, further comprising switching between said addition signal and a signal representing characteristics of said sound-producing source depending on detection of one of a no-load state and a load state.

9. An automatic sound controlling apparatus for improving accuracy of producing a canceling sound comprising:

a sound making device for outputting a compensating sound in a canceling space to cancel undesired sound from a sound-producing source;

a sound receiving device for producing an error signal that represents a difference between said compensating sound and said undesired sound;

an adaptive filter that forms a compensating signal for attenuation of said undesired sound, said compensating signal being based on said error signal produced from said sound receiving device and being supplied to the sound making device;

a prefilter provided for said adaptive filter, said prefilter equalizing frequency characteristics of at least one of a main muffler and a submuffler before forming said compensating signal;

a transfer characteristic simulator for simulating transfer characteristics in the canceling space and receiving the compensating signal from the adaptive filter;

an adder for adding the error signal and an output signal from the transfer characteristic simulator to allow an output signal of said adder to be applied to said prefilter;

a switch that alternatively feeds first and second signals to the prefilter, the first signal representing characteristics of the sound-producing source, and the second signal being an output of the adder; and a switch controller for selecting a position of said switch depending on detection of one of a no-load state and a load state.

10. The automatic sound controlling apparatus for improving the accuracy of producing the canceling sound of claim 9, further comprising a transmission controller that selects said position depending on detection of one of the no-load state and the load state.

* * * * *